United States Patent [19]

Wang et al.

[11] 4,105,631

[45] Aug. 8, 1978

[54] MULTICHROMOPHORIC ULTRAVIOLET STABILIZERS AND THEIR USE IN ORGANIC COMPOSITIONS

[75] Inventors: Richard H. S. Wang; Gether Irick, Jr., both of Kingsport, Tenn.

[73] Assignee: Eastman Kodak Company, Rochester, N.Y.

[21] Appl. No.: 802,924

[22] Filed: Jun. 2, 1977

Related U.S. Application Data

[62] Division of Ser. No. 626,521, Oct. 28, 1975, Pat. No. 4,043,973, which is a division of Ser. No. 511,570, Oct. 2, 1974, Pat. No. 3,936,419.

[51] Int. Cl.$^2$ .......................... C08K 5/45; C08K 5/34; C08K 5/15
[52] U.S. Cl. .......................... 260/45.8 A; 260/45.8 N; 260/45.8 SN; 260/45.8 NZ; 260/45.8 NT
[58] Field of Search ...................... 260/45.8 A, 45.8 N, 260/45.8 SN, 45.8 NZ, 45.8 NT

[56] References Cited

U.S. PATENT DOCUMENTS

| | | | |
|---|---|---|---|
| 3,988,295 | 10/1976 | Irick et al. | 260/45.8 NZ |
| 4,017,508 | 4/1977 | Pond | 260/45.8 N |

*Primary Examiner*—V. P. Hoke

[57] ABSTRACT

The invention relates to multichromophoric compounds which have been found to be effective ultraviolet stabilizers. The invention also relates to ultraviolet degradable organic compositions containing a stabilizing amount of the multichromophoric composition to prevent such degradation. These stabilizers are effective in the presence of other additives commonly employed in polymeric compositions including, for example, pigments, colorants, fillers, reinforcing agents and the like. These ultraviolet stabilizers may also be incorporated into the organic compositions in the polymer melt or dissolved in the polymer dope, coated on the exterior of the molded article, film or extruded fiber.

7 Claims, No Drawings

MULTICHROMOPHORIC ULTRAVIOLET STABILIZERS AND THEIR USE IN ORGANIC COMPOSITIONS

This is a division of Application Ser. No. 626,521 filed Oct. 28, 1975, now U.S. Pat. No. 4,043,973, which is a division of Application Ser. No. 511,570, filed Oct. 2, 1974, now U.S. Pat. No. 3,936,419.

This invention relates to multichromophoric ultraviolet stabilizers and their use in organic compositions. More particularly, the invention relates to multichromophoric compositions and the stabilization of ultraviolet degradable organic compositions against deterioration resulting from the exposure to such radiations with such multichromophoric compositions.

The degradative effects of ultraviolet light on various organic compositions is well known in the art. The photo-deterioration or degradation is of particular concern with organic photo-degradable compositions which are exposed to ultraviolet light, such as sunlight, for long periods of time. One group of such photo-degradable organic compositions are polymeric compositions such as polyolefins, polyesters and the like. On exposure to sunlight for extended periods of time, these polymeric compositions degrade and their physical properties are reduced to render the polymeric composition less useful for most applications. Therefore, considerable effort has been directed to providing a solution to the photo-degradation problem of polymeric compositions. As a result of this effect, there have been discovered many additives and stabilizers which improve the stability of polymeric compositions.

Moreover, various additives and stabilizers exhibit the power to absorb ultraviolet radiation within the band of 2,900 to 4,000 Å. and, when incorporated in various plastic materials such as transparent sheets, the resultant sheet acts as a filter for all the radiation passing through and will transmit only such radiations as are not absorbed by the sheet and/or the absorbing agent. It is thus possible to screen out undesirable radiations and utilize the resulting transparent sheet as a filter in many technical and commercial applications, such as wrappings for food products and the like.

While there are many additives, stabilizers and mixtures thereof which are known in the art to improve the ultraviolet light stability of organic compositions, there is a need in the art for more efficient and effective stabilizers to prevent the photo-degradation of organic compositions susceptible to photo-degradation. Therefore, to provide a more effective and efficient ultraviolet stabilizer for organic compositions susceptible to such degradation would be an advance in the state of the art.

It is, therefore, an object of the present invention to provide more effective and efficient ultraviolet light stabilizer compositions.

Another object of the present invention is to provide useful compositions characterized by improved resistance to ultraviolet degradation and deterioration.

A further object of the present invention to provide compositions containing multichromophoric compositions which are resistant to ultraviolet degradation.

Another and further object of this invention to provide processes for improving the resistance of organic materials to deterioration and degradation by actinic radiation and especially ultraviolet radiation.

A still further object of this invention to provide compositions and processes for improving the resistance of organic materials to deterioration and degradation by ultraviolet radiations, including short wavelength visible radiations.

Further objects and advantages of the invention will be apparent to those skilled in the art from the accompanying disclosure and claims.

In accordance with the present invention, multichromophoric compositions are provided which are useful as ultraviolet stabilizers or ultraviolet screening agents. These organic compositions contain at least one heterocyclic group containing composition connected to a hydroxybenzophenone, hydroxyphenylbenzotriazole or hydroxystyrene residue. The multichromophoric compositions of the present invention have the following structure:

$(A-B)_nC$ wherein A is a group having the structure:

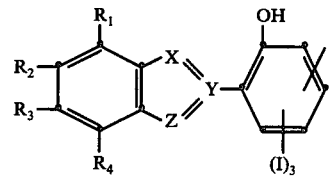

wherein

X and Y are a carbon or a nitrogen atom;

Z is an oxygen atom, a sulfur atom, a nitrogen atom, or a nitrogen atom containing a hydrogen atom or a substituted or unsubstituted alkyl group having 1 to 12 carbon atoms or an aryl group or substituted aryl group having 6 to 12 carbon atoms;

$R_1$, $R_2$, $R_3$ and $R_4$ are hydrogen, lower alkyl, substituted lower alkyl, having 1 to 12 carbon atoms, cycloalkyl, substituted cycloalkyl, aryl, substituted aryl, having 6 to 18 carbon atoms, lower alkylaryl, aryl-substituted-aryl, chloro, bromo, fluoro, aryloxy, alkoxy, substituted amino, cyano, carboalkoxy and the substituents $R_1$ and $R_2$, $R_2$ and $R_3$, and $R_3$ and $R_4$, combined with the carbon atoms to which they are attached, are joined alkylene groups completing a carbocyclic ring, which ring can also be substituted with one or more of the substituents listed above for $R_1$, $R_2$, $R_3$ and $R_4$.

I is a substituent listed above for $R_1$, $R_2$, $R_3$ and $R_4$ and is present on all positions of the benzenoid ring, except the carbon atom attached to the Y substituent and the carbon atom attached to the B group. The B connecting group is attached to the benzenoid ring in the ortho, meta or para position from the carbon atom connected to the Y substituent. The I substituents can all be one of the substituents listed above or different listed substituents.

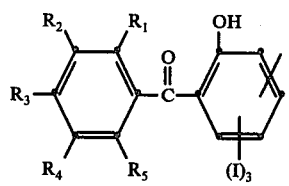

$R_1$, $R_2$, $R_3$, $R_4$ and $R_5$ are hydrogen, lower alkyl, substituted lower alkyl, having 1 to 12 carbon atoms, cycloalkyl, substituted cycloalkyl, aryl, substituted aryl having 6 to 18 carbon atoms, lower alkylaryl, aryl-substituted-aryl, chloro, bromo, fluoro, aryloxy, alkoxy, substituted amino, cyano, carboalkoxy and the substituents $R_1$ and $R_2$, $R_2$ and $R_3$, $R_3$ and $R_4$ and $R_4$ and $R_5$, combined with the carbon atoms to which they are attached, are joined alkylene groups completing a carbocyclic ring, which ring can also be substituted with one or more of the substituents listed above for $R_1$, $R_2$, $R_3$, $R_4$ and $R_5$.

I is the same substituent as listed above and is present in all positions of the benzenoid rings except the carbon atom attached to the B group connecting the A and C moieties. The B connecting group is attached to the benzenoid ring in the ortho, meta or para position from the carbonyl group of the benzophenone. The I substituents can all be one of the substituents listed above or different listed substituents; and

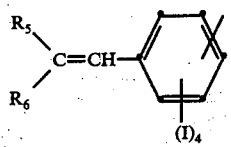

3.

$R_5$ and $R_6$ are cyano, carbonylalkoxy, carbonylaryloxy, alkylsulfonyl, arylsulfonyl, carboxamide and sulfonamide.

The B group is a group connecting A and C and can have the structure

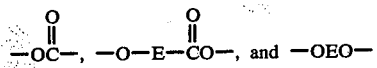

where E is lower alkylene or substituted lower alkylene.

The C group is a heterocyclic group having the structures

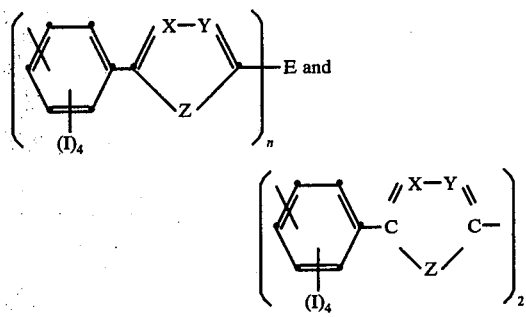

wherein

X and Y are a carbon atom or a nitrogen atom; Z is an oxygen atom, a sulfur atom, a nitrogen atom, or a nitrogen atom containing a hydrogen atom or a substituted or unsubstituted lower alkyl group having 1 to 12 carbon atoms; I is hydrogen, fluoro, chloro, bromo, lower alkyl, substituted lower alkyl, cycloalkyl, substituted cycloalkyl, aryl, substituted aryl, lower alkylaryl, arylsubstituted-aryl, alkoxy, aryloxy, substituted amino and cyano. I is present on all positions of the benzenoid ring, except the carbon atom attached to the heterocyclic group and the carbon atom attached to the B group. E is a substituted or unsubstituted alkylene and arylene. $n$ is an integer from 1 to 6.

Suitable heterocyclic A groups having the structure

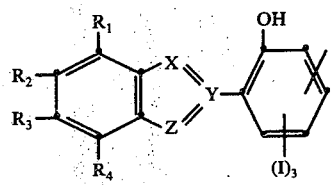

are, for example substituted and unsubstituted benzotriazoles, benzoxazoles, benzthiazoles, indoles and benzimidazoles.

Examples of suitable benzotriazoles are those having the formula

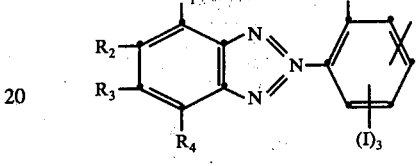

such as 4-(2H-benzotriazol-2-yl), 2-hydroxyphenyl, 4-(5-chloro-2H-benzotriazol-2-yl), 2-hydroxyphenyl, 5-(2H-benzotriazol-2-yl)-2-hydroxyphenyl, and the like.

Examples of suitable benzoxazoles are those benzoxazoles having the formula

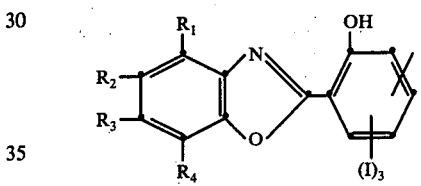

such as 4-(5,6-dimethyl-2-benzoxazolyl)-2-hydroxyphenyl, 4-(2-benzoxazolyl)-2-hydroxyphenyl, 5-(5-chloro-2-benzoxazolyl)-2-hydroxyphenyl, and the like.

Examples of suitable benzthiazoles are those having the formula

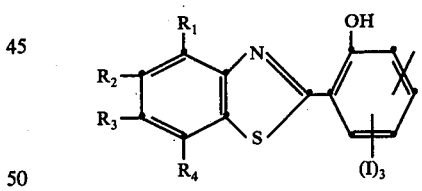

such as 4-(5,6-dimethyl-2-benzthiazolyl)-2-hydroxyphenyl, 4-(2-benzthiazolyl)-2-hydroxyphenyl, 5-(5-chloro-2-benzthiazolyl)-2-hydroxyphenyl, and the like.

Examples of suitable benzimidazoles are those having the formula

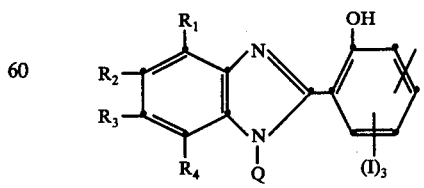

wherein Q is hydrogen or lower alkyl group containing 1 to 12 carbon atoms or aryl group or substituted aryl group having 6 to 18 carbon atoms. Such suitable benzimidazole moieties are, for example, 4-(5,6-dimethyl-2-benzimidazolyl)-2-hydroxyphenyl, 4-(2-benzimidazolyl)-2-hydroxyphenyl, 5-(5-chloro-2-benzimidazolyl)-2-hydroxyphenyl, 4-(1-methyl-2-benzimidazolyl)-2-hydroxyphenyl, 4-(1-ethyl-5-chloro-2-benzimidazolyl)-2-hydroxyphenyl and the like.

Suitable A groups having the structure

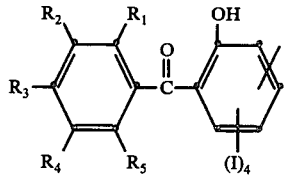

are, for example, 2-hydroxybenzophenone moieties, such as 3-hydroxy-4-benzoylphenyl, 3-hydroxy-4-(2-hydroxybenzoyl) phenyl, 3-hydroxy-4-(2-hydroxy-4-methoxybenzoyl) phenyl, 3-hydroxy-4-(4-chlorobenzoyl) phenyl, 3-hydroxy-4-(3,5-dimethylbenzoyl) phenyl, 3-hydroxy-4-(4-methoxybenzoyl) phenyl, 3-hydroxy-4-(4-cyanobenzoyl) phenyl, 3-hydroxy-4-benzoyl-6-methylphenyl, and 3-hydroxy-4-benzoyl-6-chlorophenyl.

Suitable A groups having the structure

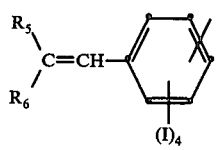

are, for example, disubstituted sytrene moieties such as 4-(2,2-dicyanovinyl) phenyl, 4-(2,2-di-carbomethoxyvinyl) phenyl, 4-(2-cyano-2-carbobutoxyvinyl) phenyl, 4-(2-phenylsulfonyl-2-carboethoxyvinyl) phenyl, 4-(2-cyano-2-carboxamidovinyl) phenyl, 4-(2-acetyl-2-cyanovinyl) phenyl, 4-(2-benzoyl-2-cyanovinyl) phenyl, 4-(2-benzoyl-2-carbomethoxyvinyl) phenyl, 4-(2,2-dicyanovinyl)-2-chlorophenyl, 4-(2,2-dicyanovinyl)-2-methylphenyl, and 4-(2,2-dicyanovinyl)-3-methylphenyl.

Suitable B groups are oxycarbonyl, oxyalkylene carbonyloxy, for example, oxymethylene carbonyloxy and the like, oxyalkyleneoxy, for example, oxyethyleneoxy and the like.

Suitable C groups are, for example, moieties having the structures:

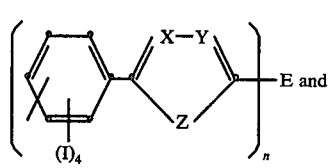

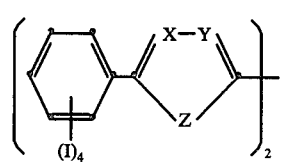

and include substituted and unsubstituted 1,3,4-oxadiazol-2,5-diyl, 1,3,4-thiadiazol-2,5-diyl, 1,2,4-triazol-3,5-diyl, oxazol-diyl, thiazoldiyl and imidazoldiyl and the like.

Examples of suitablt 1,3,4-oxadiazol-2,5-diyl moieties are those having the structures:

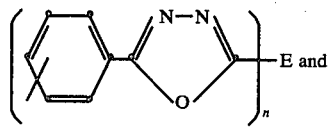

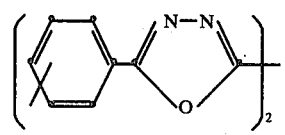

wherein E is a substituted or unsubstituted, branched or unbranched alkylene having 1 to 12 carbon atoms or arylene having 6 to 18 carbon atoms; n is an integer from 1 to 6; such as 4,4'-(1,3,4-oxadiazol-2,5-diyl)diphenyl, 4,4'[5,5'-tetramethylene bis(1,3,4-oxadiazol-2-yl)]diphenyl, 4,4'-[5,5'-bis(1,3,4-oxadiazol-2,2'-diyl)-]diphenyl, 4,4'-[5,5'-m-phenylene bis(1,3,4-oxadiazol-2-yl)]diphenyl, 4,4',4"-[5,5',5"-(1,3,5-phenylene tris(1,3,4-oxadiazol-2-yl)triphenyl and the like.

Examples of suitable 1,3,4-thiadiazol-2,5-diyl moieties are those having the structures:

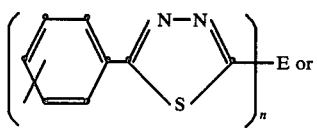

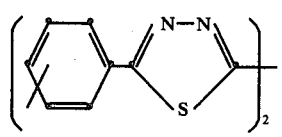

wherein E is a substituted or unsubstituted alkylene or arylene; n is an integer from 1 to 6; such as 4,4'-(1,3,4-thiazol-2,5-diyl)diphenyl, 4,4'-(5,5'-tetramethylene bis(1,3,4-thiadiazol-2-yl)diphenyl, 4,4'-[5,5'-bis(1,3,4-thiadiazol-2,2'-diyl)]diphenyl, 4,4'-[5,5'-m-phenylene bis(1,3,4-thiadiazol-2-yl)]diphenyl, 4,4',4"-[5,5',5"-(1,3,5-phenylene tris(1,3,4-oxadiazol-2-yl) triphenyl and the like.

Examples of suitable 1,2,4-triazol-3,5-diyl moieties are those having the structures:

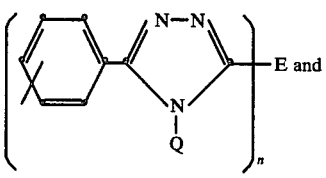

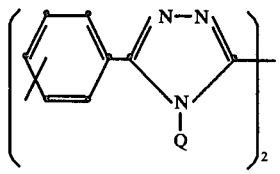

wherein E is a substituted or unsubstituted alkylene and arylene; n is an integer from 1 to 6, Q is hydrogen or a substituted or unsubstituted lower alkyl group containing 1 to 12 carbon atoms; such as 4,4'-(1H-1,2,4-triazol-3,5-diyl)diphenyl, 4,4'(4H-1,2,4-triazol-3,5-diyl)diphenyl, 4,4'-[5,5'-tetramethylene bis(4H-1,2,4-triazol-3-yl)]diphenyl, 4,4'-(4-methyl-1,2,4-triazol-3,5-diyl)diphenyl, 4,4'-(1-methyl-1,2,4-triazol3,5-diyl)diphenyl, 4,4'-[5,5'-m-phenylene bis(4-methyl-1,2,4-triazol-3-yl)]diphenyl, and the like.

Examples of suitable oxazol-diyl moieties are those having the structures:

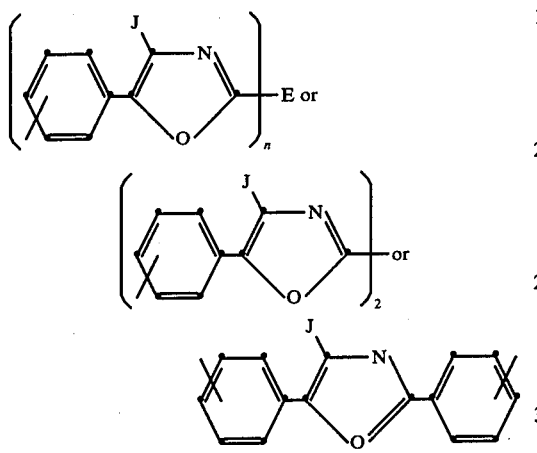

wherein E is a substituted or unsubstituted alkylene and arylene, or the same as $R_1$; J is the same as $R_1$ or a substituted or unsubstituted alkylene or arylene; n is an integer from 1 to 6; such as 4,4'-(oxazol-2,5-diyl)diphenyl, 4,4'-(methyloxazol-2,5-diyl)diphenyl, 4,4'-(4-phenyloxazol-4,5-diyl)diphenyl, 3,4'-(4-methyloxazol-2,5-diyl)diphenyl and the like.

Examples of suitable thiazol-diyl moieties are those having the structures:

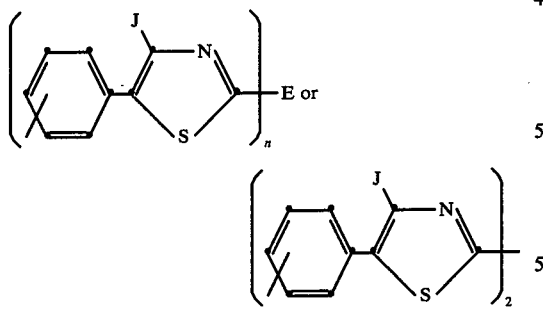

wherein E is a substituted or unsubstituted alkylene and arylene, or the same as $R_1$; J is the same as $R_1$ or a substituted or unsubstituted alkylene or arylene; n is an integer from 1 to 6; such as 4,4'-(thiazol-2,5-diyl)diphenyl, 4,4'-(4-methylthiazol-2,5-diyl)diphenyl, 4,4'-(2-methylthiazol-4,5-diyl)diphenyl, 4,4'-(thiazol-4,5-diyl)diphenyl, and the like.

Examples of suitable imidazol-diyl moieties are those having the structures:

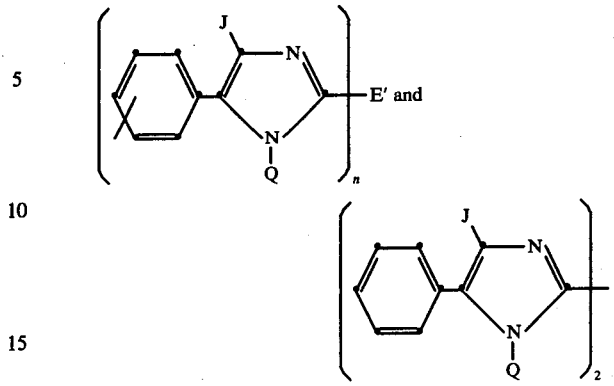

wherein E' is a substituted or unsubstituted alkylene and arylene, or the same as $R_1$; J is the same as $R_1$, or a substituted or unsubstituted alkylene or arylene; n is an integer from 1 to 6; Q is hydrogen or a substituted or unsubstituted lower alkyl group having 1 to 12 carbon atoms, such as 4,4'-(imidazol-2,5-diyl)diphenyl, 4,4-(1-methylimidazol-2,5-diyl)diphenyl, 4,4'-(2-methylimidazol-4,5-diyl)diphenyl, 4,4'-(4-methylimidazol-2,5-diyl)diphenyl, 4,4'-(1,4-dimethylimidazol-2,5-diyl)diphenyl and 4,4'-(1,2-dimethylimidazol-4,5-diyl)diphenyl and the like.

The heterocyclic compositions can be added to organic compositions which are susceptible to ultraviolet degradation. Such compositions include, for example, polymeric compositions such as polyester fiber and molding compositions, such as polyethylene terephthalate, polytetramethylene terephthalate and the like; polyolefins such as, for example, high, medium and low density polyethylene, polypropylene, polybutene and the like; polyamides such as N-methoxymethyl polyhexamethylene adipamide and the like; polycarbonates; polyvinyl chlorides and copolymers; cellulose esters; acrylic/butadiene/styrene plastic; polyacrylics such as methyl methacrylate; polystyrene; gelatin; vinylidene chloride copolymers such as vinylidene chloride/vinyl acetate copolymers; ethylene vinyl acetate copolymers; cellulose ethers such as methyl cellulose; polyvinyl esters such as polyvinyl acetate; polyethylene oxide; polyvinyl acetals; polyformaldehydes; and polyurethanes. Such compositions also include natural and synthetic rubbers, such as polybutadiene, and unsaturated organic compositions such as oils and the like, as well as compositions containing such organic compositions.

The multichromophoric compositions, as effective ultraviolet stabilizers or screening agents, are generally used in an amount of from 0.01 to 10%, by weight, based on the weight of the organic material to which they are added. While a detectable amount of ultraviolet screening and stabilization may be obtained with amounts less than 0.01%, this amount of stabilization or screening would be of little practical utility in a commercial application. Moreover, while amounts greater than 10%, by weight, provide effective ultraviolet stability and screening, such concentrations are undesirable because of cost and the deleterious effect which such concentrations may have on the mechanical properties of the organic composition in which the stabilizer is incorporated. Preferably, the stabilizer is used in an amount of from about 0.1 to about 3%, by weight. For example, an amount of 2%, by weight, of the stabilizer effectively stabilizes cellulose acetate butyrate plastic compositions.

The ultraviolet stabilized organic compositions of the present invention may also contain other additives, pigments, colorants, stabilizers and the like. For example, polymeric compositions, such as polyolefins, may also contain and generally do contain other additives such as white or colored pigments or colorants, antioxidants, plasticizers, flow aids, processing aids, polymeric modifiers and the like.

These novel multichromophoric ultraviolet stabilizers may be incorporated into organic compositions by melt-blending or may be added onto the surface of an organic plastic material prior to being molded into a suitable object. These materials can also be added to coatings and the like which can be applied to the surface of a molded object.

This invention will be further illustrated by the following examples although it will be understood that these examples are included merely for purposes of illustration and are not intended to limit the scope of the invention.

EXAMPLE 1

Bis(4-benzoyl-3-hydroxylphenyl) 4,4'-(1,3,4-oxadiazol-2,5-diyl)dibenzoate, I, can be prepared by the following procedure:

To a solution of hydrazine (0.09 mole) and sodium bicarbonate (15 g.) in 150 ml. of water, monoterephthaloyl chloride (0.18 mole) in 125 ml. of THF was added slowly with stirring. After stirring for an additional 30 in., the product A was filtered and washed with 1 l. of water (m.p. 295°-298°, quantitative yield). A solution of A (0.056 mole) and 100 ml. of phosphorus oxychloride in 200 ml. of toluene was refluxed for 6 hr. The product B was filtered and washed with water (m.p. 268°-270°, yield 80%). A solution of B (0.042 mole) and potassium hydroxide (0.1 mole) in 700 ml. of 60% ethanol was refluxed for 10 hr. The mixture was then acidifed with 6N hydrochloric acid. The product was filtered and identified as the corresponding bis acid (m.p. >300° C., quantitative yield). The bis acid (0.013 mole) was refluxed with 50 ml. of thionyl chloride in 200 ml. of chlorobenzene for 10 hours. After removal of excess thionyl chloride, the product C was obtained by filtration (m.p. 208°-210°, yield 90%). To a solution of 2,4-dihydroxybenzophenone (0.023 mole) and sodium hydroxide (0.023 mole) in 50 ml. of water, C (0.016 mole) in 150 ml. of chloroform was added. The mixture was refluxed for 4 hours. After cooling, product I was obtained by filtration (m.p. 268°-273°, 70% yield).

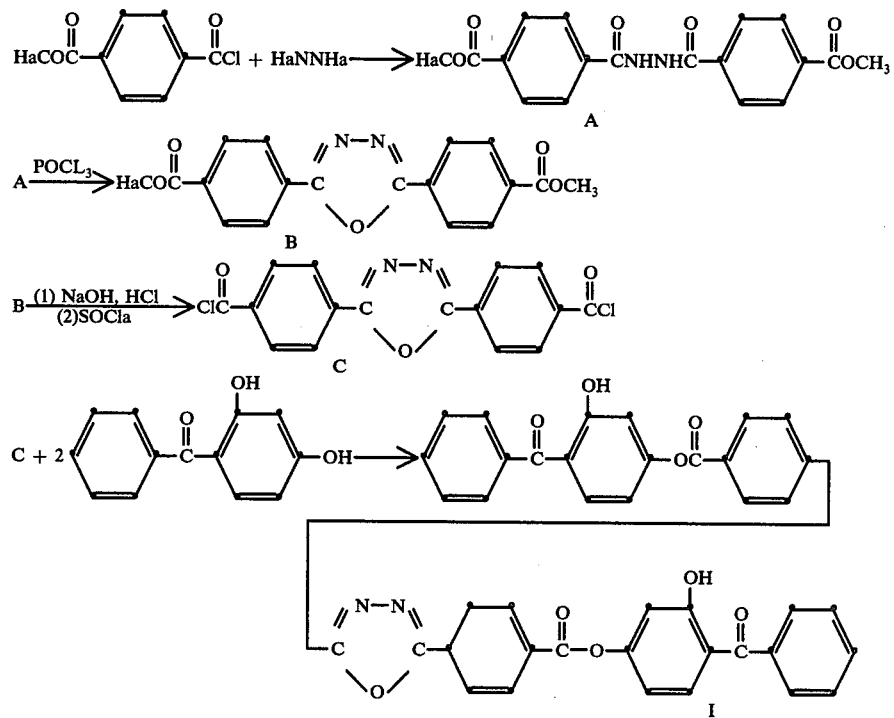

Other novel multichromophoric compounds can be prepared by substituting other orthohydroxy compounds such as bis[4-(2-cyano-2-carboethoxyvinyl)phenyl], 4,4'-(1,3,4-oxadiazol-2,5-diyl)dibenzoate, II (m.p. >82°-88°, yield 80%); bis[4-(2,2-dicarboethoxyvinyl)phenyl], 4,4'-(1,3,4-oxadiazol-2,5-diyl)dibenzoate, III (m.p. 160°-165°, yield 50%); bis [4-(2H-benzotriazol-2-yl)-3-hydroxyphenyl]-4,4'-(1,3,4-oxadiazol-2,5-diyl)-dibenzoate, IV (m.p. >300°, yield 50%); and bis[4-(2-benzoxazolyl)-3-hydroxyphenyl]-4,4'-(1,3,4-oxadiazol-2,5-diyl)dibenzoate and the like.

EXAMPLE 2

Bis[4-[2-[4,4'-(1,3,4-oxadiazol-2,5-diyl)diphenoxy]ethoxy]-2-hydroxybenzophenone], V, can be prepared by the following procedure:

2,5-Bis(p-hydroxyphenyl)-1,3,4-oxadiazole, prepared as in Makromol. Chem., 95, 261 (1966), was refluxed with 4-(2-bromoethoxy)-2-hydroxybenzophenone and potassium carbonate in butanone for 10 hours. The product was obtained after removal of solvent and crystallized from toluene (m.p. 165°-170°, yield 50%).

Other novel multichromophoric compounds can be prepared by substituting other ortho-hydroxy compounds such as bis[4-[2-[4,4'-(1,3,4-oxadiazol-2,5-diyl)- diphenoxy]ethoxy]-2-(2-hydroxyphenylbenzotriazole)]; and bis[4-[2-[4,4'-(1,3,4-oxadiazol-2,5-diyl)diphenoxy]ethoxy]-β-cyano-b-carboethoxystyrene] and the like.

EXAMPLE 3

Bis[4-benzoyl-3-hydroxyphenyl)4,4'-(4-methyl-1,2,4-triazol-3,5-diyl)dibenzoate, VI, can be prepared by the following procedure:

A solution of N-methyl-p-carbomethoxybenzamide in chloroform was treated with phosphorus pentachloride to give D. Then D was reacted with p-carbomethoxybenzoyl hydrazide to yield dimethyl-4,4'-(4-methyl-1,2,4-triazol-3,5-diyl)dibenzoate, (E). The VI was obtained by reacting F in a similar manner as in Example 1.

EXAMPLE 4

Bis[4-benzoyl-3-hydroxyphenyl)4,4'-(5,5'-bi-1,3,4-oxadiazol-2,2'-diyl)dibenzoate], VII, can be prepared by the following procedure:

A mixture of oxalyl dihydrazide (0.01 mole), lithium chloride (2.0 g.) and p-carbomethoxybenzoyl chloride (0.02 mole) in N-methyl pyrrolidinone (100 ml.) was stirred at room temperature for 15 hours. The mixture was poured into 500 ml. of ice water. The product, 1,1'-oxalylbis[2-(p-carbomethoxybenzoyl)hydrazine, F, was obtained by filtration. Then VII was produced by reacting F in a similar manner as in Example 1.

EXAMPLE 5

Bis[4-benzoyl-3-hydroxyphenyl)4,4'-(4-methyloxazol-2,5-diyl)-dibenzoate, VIII, can be produced by the following procedure:

α-(p-Carbomethylbenzamido)-p-carbomethoxypropiophenone, obtained by reacting p-carbomethoxybenzamide with α-bromo-p-carbomethoxypropiophenone, was refluxed with phosphorus oxychloride in toluene to yield dimethyl-4,4'-(4-methyloxazol-2,5-diyl)dibenzoate, G. The VIII was obtained in a similar manner as in Example 1.

EXAMPLE 6

Bis[4-benzoyl-3-hydroxyphenyl)-4,4'-(2-methyloxazol-4,5-diyl)dibenzoate, IX, can be produced by the following procedure:

p,p'-Dicarbomethoxybenzoin, obtained by benzoin condensation of methyl p-formylbenzoate, was refluxed with ammonium acetate, paraldehyde in glacial acetic acid for 2 hours. The product, dimethyl-4,4'-(2-methyloxazol-4,5-diyl)dibenzoate, H, was obtained by filtration after cooling. Then IX was obtained in a similar manner as in Example 1.

EXAMPLE 7

The ultraviolet stabilization provided by the heterocyclic compound of the present invention is shown for poly(tetramethylene terephthalate) in Table 1.

A dry mixture of the stabilizer and granulated poly(tetramethylene terephthalate) were extruded into 1/16-inch diameter rods, pelletized and injection molded into 2½- × ½- × 1/16-inch flat bars; these flat bars were exposed to a 280–700 nm. mercury lamp source until a flatwise impact strength of less than 6 was obtained (initial values were all >17).

The text results are summarized in Table 1.

Table 1

| Effectiveness of Ultraviolet Stabilizers in Poly(tetramethylene terephthalate) | | | |
|---|---|---|---|
| | | FWIS (Flatwise Impact Strength) | |
| Compound (0.5%) | Initial | 300 hr. | 500 hr. |
| None | 17 | 6 | 1 |
| I | 19 | 20 | 20 |
| II | 20 | 21 | 18 |
| III | 20 | 21 | 20 |
| IV | 18 | 18 | 16 |
| V | 19 | 20 | 18 |
| VI | 19 | 19 | 18 |
| VII | 20 | 20 | 19 |
| VIII | 18 | 18 | 16 |
| IX | 19 | 18 | 18 |

These multichromophoric compositions find particular utility as ultraviolet stabilizers in organic compositions requiring ultraviolet stability. Such compositions include polymeric compositions such as, for example, polyester fiber and molding compositions, poly-α-olefins, polyamides, acrylics, cellulose esters and the like, as well as molded or shaped articles, film and coatings formed from such materials and the like. Such compositions also include natural and synthetic rubbers, such as natural rubber, as well as organic materials such as oils, fats, and unsaturated organic materials and materials having such materials contained therein such as paints, varnishes, cosmetics and the like.

The invention has been described in detail with particular reference to preferred embodiments thereof, but it will be understood that variations and modifications can be effected within the spirit and scope of the invention.

We claim:

1. An organic composition susceptible to ultraviolet degradation stabilized against such degradation with a stabilizing amount of a composition of matter comprising compounds having the formula:

$(A-B)_2 C$ wherein A is a group having the structure

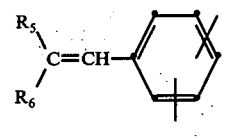

I wherein
I is hydrogen, fluoro, chloro, bromo, lower alkyl, substituted lower alkyl, cycloalkyl, substituted cycloalkyl, aryl, substituted aryl, lower alkylaryl, alkoxy, aryloxy, substituted amino, cyano, or carboalkoxy;

$R_5$ and $R_6$ are cyano, carbonylalkoxy, carbonylaryloxy, alkylsulfonyl, alkylcarbonyl, arylsulfonyl, arylcarbonyl, carboxamide or sulfonamide;

B is a linking group connecting A and C and can have the structure

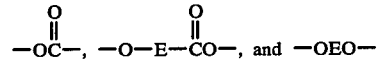

where E is lower alkylene or substituted lower alkylene;

C group is a heterocyclic group having the structure

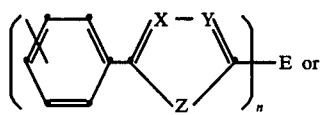

wherein

X and Y are a carbon atom, a carbon atom containing an alkyl group containing 1 to 12 carbon atoms, a carbon atom containing an aryl group containing 6 to 18 carbon atoms, or a nitrogen atom; Z is an oxygen atom, a sulfur atom, or a nitrogen atom containing a hydrogen atom or a substituted or unsubstituted lower alkyl group having 1 to 12 carbon atoms; E is a substituted or unsubstituted, branched or unbranched alkylene containing 1 to 12 carbon atoms or arylene containing 6 to 18 carbon atoms; and n is an integer from 1 to 6.

2. An organic composition according to claim 1 containing a stabilizing amount of a composition of matter having the formula:

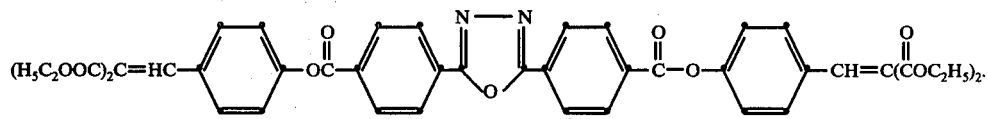

3. An organic composition according to claim 1 containing a stabilizing amount of a composition of matter having the formula:

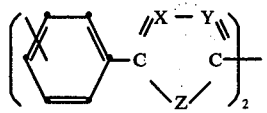

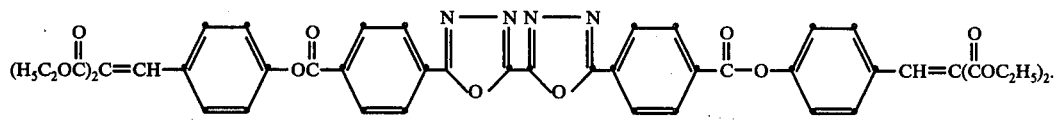

4. An organic composition according to claim 1 containing a stabilizing amount of a composition of matter having the formula:

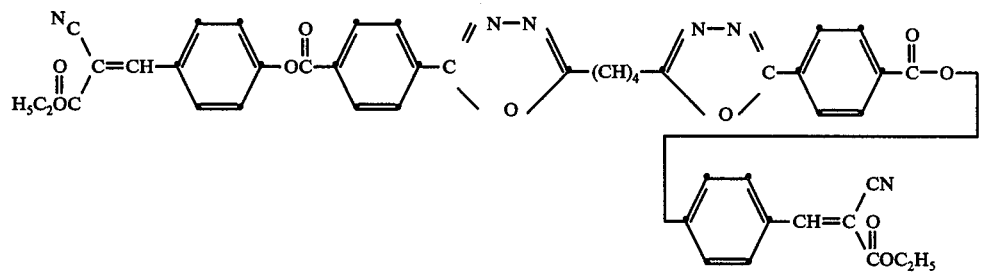

5. An organic composition according to claim 1 containing a stabilizing amount of a composition of matter having the formula:

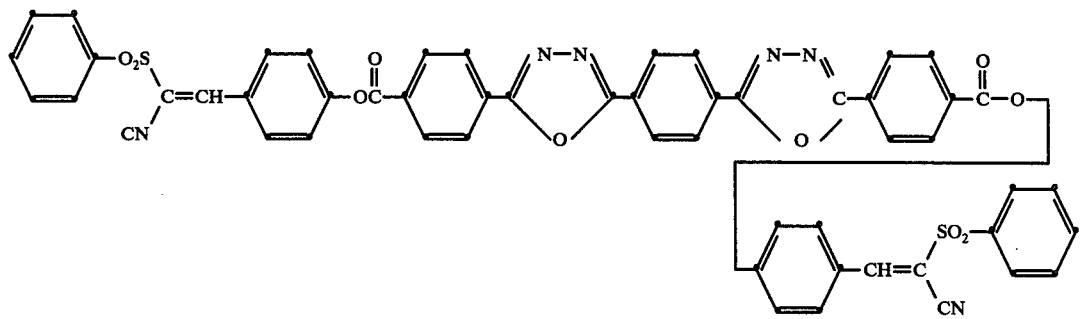

6. An organic composition according to claim 1 containing a stabilizing amount of a composition of matter having the formula:

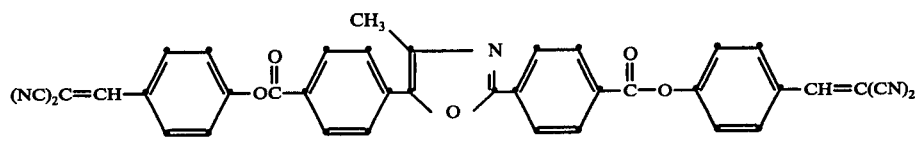
7. An organic composition according to claim 1 containing a stabilizing amount of a composition of matter having the formula:
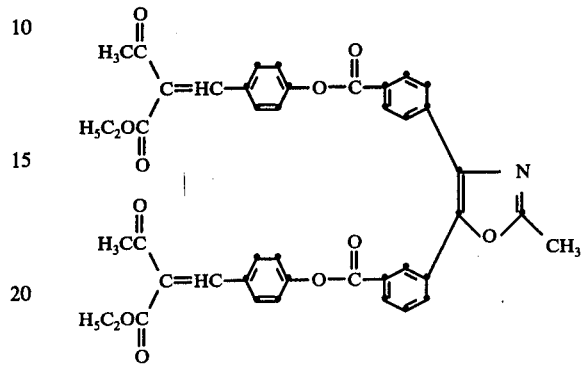
* * * * *

UNITED STATES PATENT AND TRADEMARK OFFICE
CERTIFICATE OF CORRECTION

PATENT NO. : 4,105,631
DATED : August 8, 1978
INVENTOR(S) : Richard H.S. Wang and Gether Irick, Jr.

It is certified that error appears in the above-identified patent and that said Letters Patent are hereby corrected as shown below:

Column 12, lines 43-48, delete the formula and insert therefor

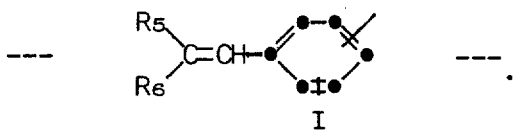

Signed and Sealed this

Twenty-third Day of January 1979

[SEAL]

Attest:

RUTH C. MASON
Attesting Officer

DONALD W. BANNER
Commissioner of Patents and Trademarks